United States Patent
Bouffier

(10) Patent No.: US 7,713,188 B2
(45) Date of Patent: May 11, 2010

(54) SURGICAL DEVICE FORMING A SURGICAL PROSTHESIS

(75) Inventor: Bernard Bouffier, Ecole (FR)

(73) Assignee: La Societe Evergin SA, Lausanne (FR)

(*) Notice: Subject to any disclaimer, the term of this patent is extended or adjusted under 35 U.S.C. 154(b) by 700 days.

(21) Appl. No.: 11/615,144

(22) Filed: Dec. 22, 2006

(65) Prior Publication Data
US 2007/0162120 A1 Jul. 12, 2007

Related U.S. Application Data

(60) Provisional application No. 60/804,972, filed on Jun. 16, 2006.

(30) Foreign Application Priority Data

Dec. 26, 2005 (FR) .................................. 05 54088

(51) Int. Cl.
*A61F 2/00* (2006.01)
(52) U.S. Cl. .............................. 600/37; 600/29; 600/30
(58) Field of Classification Search .................. 600/29, 600/30, 37
See application file for complete search history.

(56) References Cited

U.S. PATENT DOCUMENTS

| | | | |
|---|---|---|---|
| 5,954,057 A * | 9/1999 | Li .............................. | 128/898 |
| 6,068,591 A * | 5/2000 | Bruckner et al. .............. | 600/30 |
| 6,110,101 A | 8/2000 | Tihon et al. | |
| 6,599,318 B1 * | 7/2003 | Gabbay .................... | 623/11.11 |
| 2002/0161382 A1 * | 10/2002 | Neisz et al. ................. | 606/151 |
| 2003/0023137 A1 * | 1/2003 | Gellman ...................... | 600/30 |
| 2003/0065402 A1 * | 4/2003 | Anderson et al. ......... | 623/23.66 |
| 2003/0191360 A1 * | 10/2003 | Browning .................... | 600/29 |
| 2004/0015048 A1 | 1/2004 | Neisz et al. | |
| 2004/0106847 A1 * | 6/2004 | Benderev ..................... | 600/37 |
| 2006/0089525 A1 * | 4/2006 | Mamo et al. .................. | 600/37 |

FOREIGN PATENT DOCUMENTS

WO 2004/004600 X 1/2004

* cited by examiner

*Primary Examiner*—Charles A Marmor, II
*Assistant Examiner*—Catherine E Burk
(74) *Attorney, Agent, or Firm*—Lucas & Mercanti, LLP

(57) ABSTRACT

The surgical device is for supporting a mammalian organ in need of support, and in particular for treating urinary incontinence. The device has at least one first support element of elongate shape for exerting a supporting action on the organ; and at least one first traction filiform element, to be fastened to the support element. One end of the traction element constituting at least one first anchor system, activated by traction exerted on the first traction element thereby simplifying the surgical procedure.

33 Claims, 8 Drawing Sheets

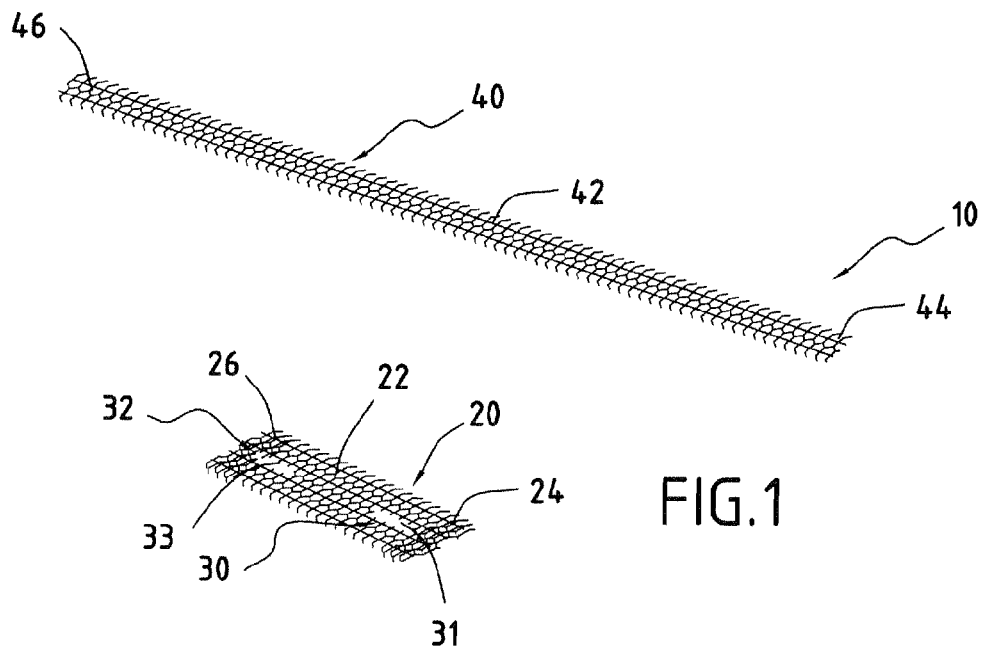
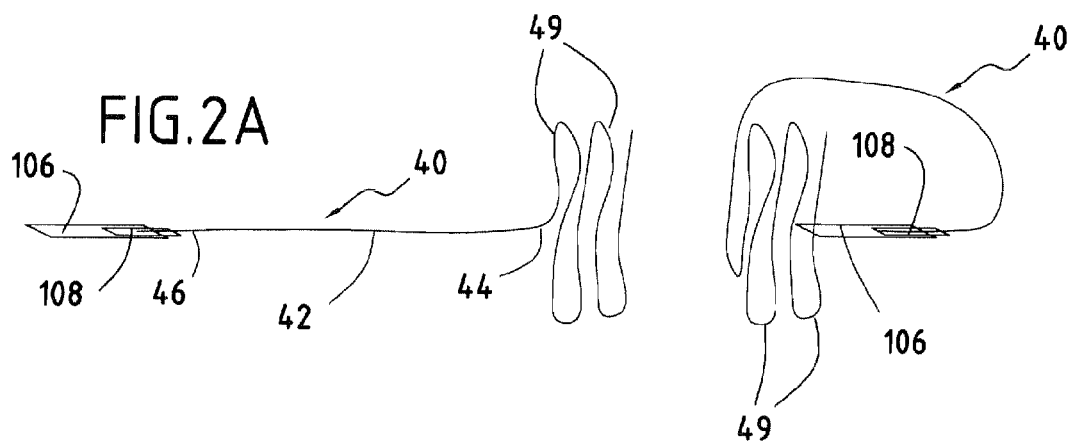
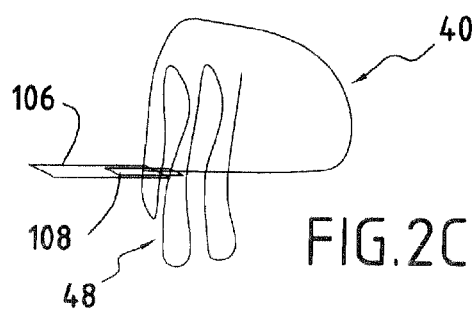

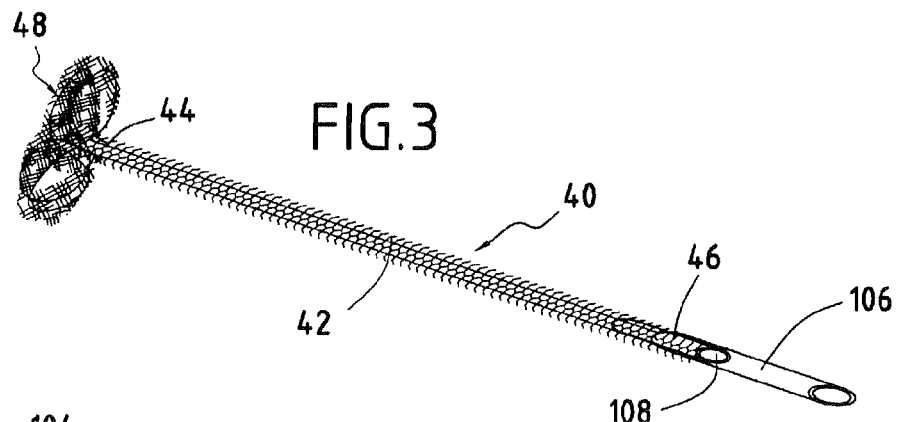
FIG.3
FIG.4
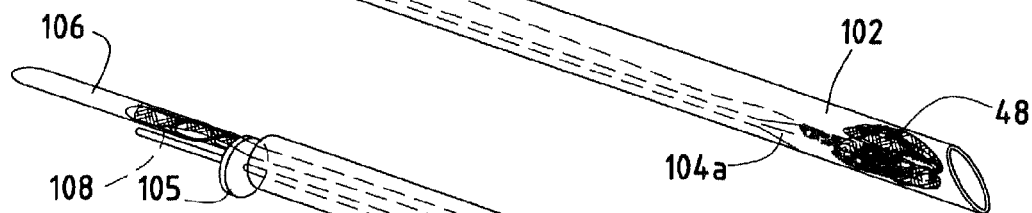
FIG.5
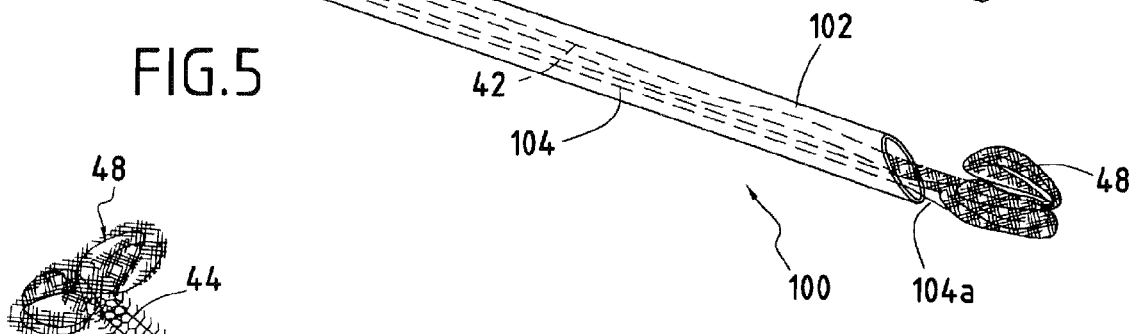
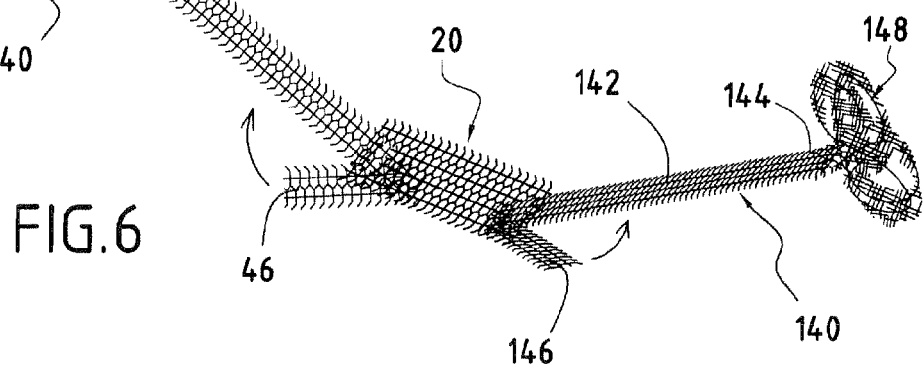
FIG.6

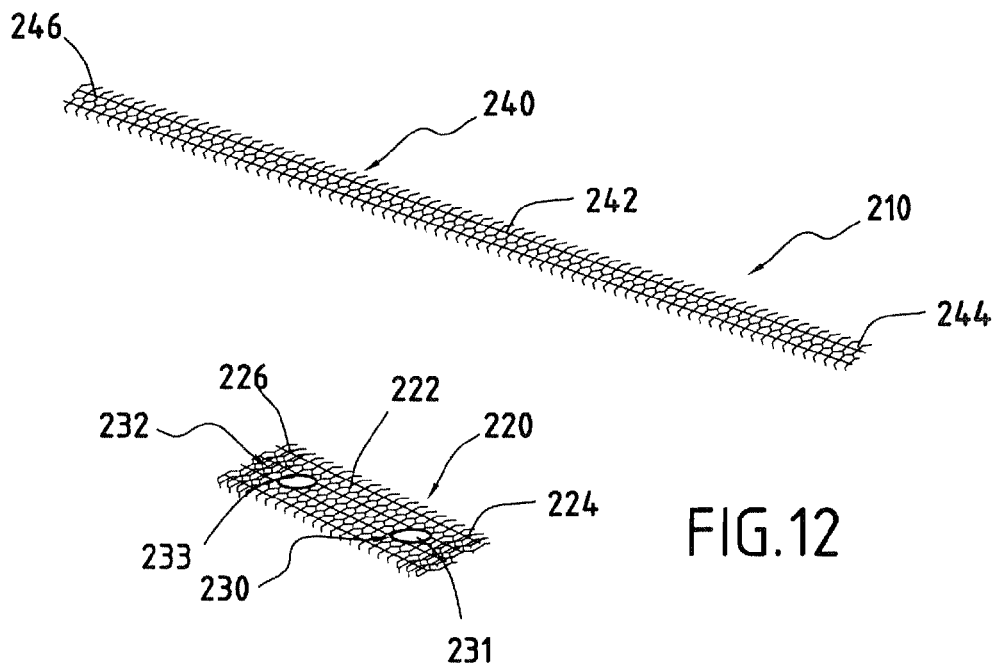
FIG.12
FIG.13
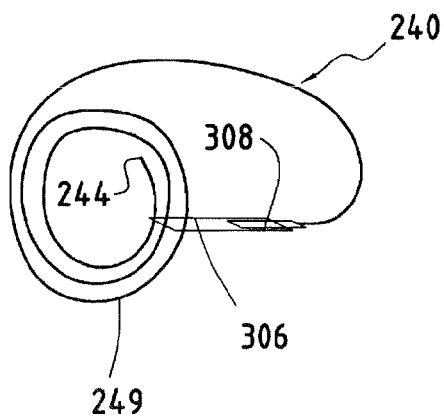
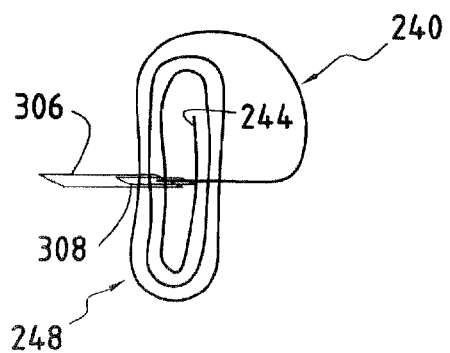
FIG.13A

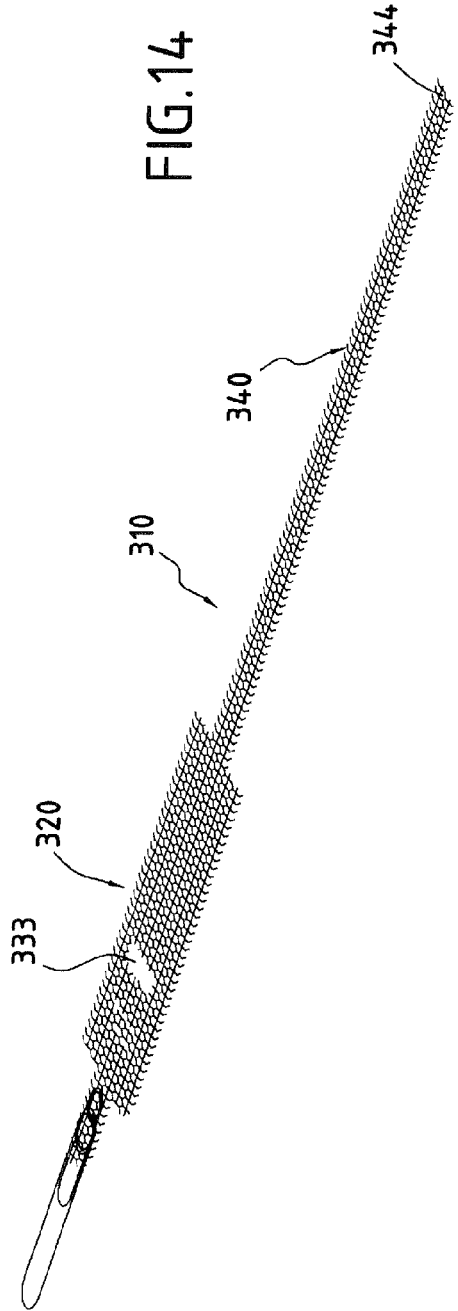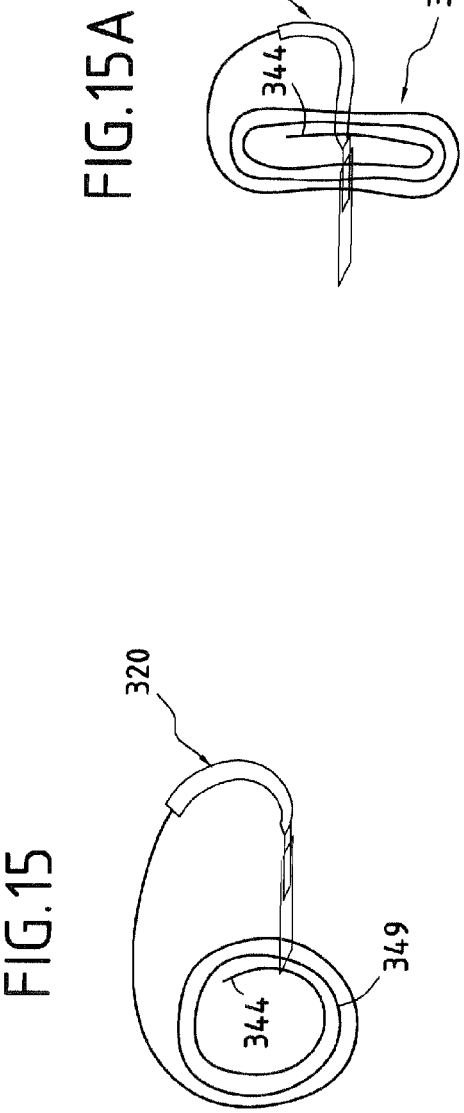

SURGICAL DEVICE FORMING A SURGICAL PROSTHESIS

This application claims the priority of U.S. Provisional Patent Application No. 60/804,972 filed on Jun. 16, 2006 and French Patent Application No. FR 05.54088 filed on Dec. 26, 2005, the contents of which are incorporated herein by reference.

The present invention relates essentially to a surgical device forming a surgical prosthesis for implanting to support an organ in a mammal.

FIELD OF THE INVENTION

In the context of the invention, any mammalian organ for which support can be provided is capable of being treated by the surgical device of the invention.

The invention is particularly adapted to supporting organs of the pelvis, the urethra, the bladder, the vagina, the cervix of the uterus, the uterus, and the rectum.

The invention relates preferably to a surgical device forming a surgical prosthesis for providing urethral support for treating urinary incontinence, in particular in a female mammal, preferably a woman, or a male mammal, preferably a man. Preferably, this device has to be sufficiently versatile to be usable without significant modification both in the male and female urinary continence.

Thus, the surgical prosthesis-forming device of the present invention is designed to fix or hold various organs or tissues, possibly also providing more significant modifications, as might be required by anatomical or pathological conditions.

STATE OF THE ART

It is known that stress urinary incontinence is the consequence of the urethra being excessively mobile when a large amount of abdominal pressure is applied, as can be caused by coughing, laughing, running, and more generally by applying abdominal thrust.

Leaks of urine occur more easily and more abundantly with increasing mobility of the urethra, or with the canal being permanently subject to ptosis.

Incontinence can be associated with the pelvic organs (vagina, uterus, bladder, rectum) being prolapsed to varying extents. It can be isolated. It is nearly always the more or less delayed consequence of giving birth by vaginal delivery. It constitutes a dreadful infirmity, painfully restricting the freedom and the dignity of mothers and men. It is frequently kept secret, which makes it difficult to study its morbidity.

In an earlier invention of the present inventor, published under the No. FR-A-2 843 876=US-A-2005-0261547, proposals have already been made for a surgical device comprising a cage-forming fixing device co-operating with a traction wire itself secured to a support element in the form of a strip, clearly visible in FIGS. 1 and 3 of that document. While it is in the folded state, the cage-forming fixing device is introduced with the help of a trocar above the transverse pelvic wall, and after the trocar has been withdrawn, and after the device has been deployed, traction on the traction wire causes the cage to be flattened, thereby taking up a flat shape providing a large bearing area against the pelvic wall, and thus providing fixing against the pelvic wall that is certain and reliable without any risk of tearing over time.

The functional results of that device constitute a significant improvement compared with earlier technical solutions, since it limits or almost completely limits risks of severe complications.

However, it has been found that the cage system is relatively expensive to fabricate, and requires practitioners to be trained in order to be able to put it into place properly, particularly during the difficult stage of deploying the cage and flattening it by applying traction to the traction wire.

OBJECTS OF THE INVENTION

A main object of the present invention is to solve the novel technical problem consisting in providing a surgical device forming a central prosthesis for fixing and supporting a biological organ, in particular for supporting the urethra in order to treat urinary incontinence, in particular in a female mammal, preferably a woman, or in a male mammal, preferably a man, which device is less aggressive than prior devices, is small in size, and uses fewer parts, thus being simpler in design.

Another main object of the present invention is to solve the novel technical problem specified above with a surgical device that is particularly adapted to supporting pelvic organs, the urethra, the bladder, the vagina, the cervix of the uterus, the uterus, and the rectum, both for females and males.

Another main object of the present invention is to solve these novel technical problems by means of a device that enables a surgical method of fixing and support to be implemented using a simple operating procedure, requiring a small number of steps that can be performed quickly under local anesthetic, without hospitalization, and without postoperative immobilization, i.e. it can be performed on an "outpatient" basis.

The invention makes it possible for the first time to solve these technical problems in a manner that is simple, reliable, inexpensive, and reproducible on an industrial and medical scale, by facilitating the surgical procedure making it possible for intervention to be simplified, fast, under local anesthetic, without hospitalization, and without postoperative immobilization, both for females and males.

DESCRIPTION OF THE INVENTION

Thus, in a first aspect, the present invention provides a surgical device forming a surgical prosthesis, for supporting a mammalian organ in need of support, in particular for treating urinary incontinence, the device comprising:

a) at least one first support element comprising an element of elongate shape defining a first end and a second end for exerting a supporting action on said organ; said first element of elongate shape being made at least in part out of a material that is substantially non-extensible, flexible, and deformable; and b) at least one first traction element, advantageously a filiform element, defining a first end referred to as a distal end and a second end referred to as a proximal end, which elements can be fastened by said proximal end at least temporarily to at least one end of said first elongate support element, said distal end being provided to constitute at least one first fixing or anchor system, activated by traction exerted on the first traction element, in particular at its proximal end;

said fixing system provided at the distal end of the traction element comprises at least one fold, preferably a plurality of folds, in the traction element which, when traction is exerted on the traction element, becomes deformed or flattened so as to deploy while imitating an umbrella effect so as to define an area that is sufficient for fixing or anchoring. A fixing or anchor area that is said to be "sufficient" is an area that ensures certain and reliable fixing or anchoring of the distal end of the first traction element against the tear-resistant tissue or wall of the mammalian body, without risk of tearing said wall or said tissue during said traction, or over time while the mammal leads a life without taking special precautions.

In another advantageous embodiment of the invention, the first traction element is also made at least in part out of a material that is substantially non-extensible, flexible, and deformable. In a particular variant embodiment, the first traction element may be made out of the same material as that used for making the first support element.

In another advantageous embodiment of the invention, it is possible to provide a second traction element, preferably of the same design as the first traction element, and is thus likewise filiform, likewise defining a distal first end and a proximal second end, being suitable for being fastened by said proximal end at least temporarily to at least one other end of said first elongate support element, said distal end of the second traction element being also provided to constitute at least one second fixing or anchor system against another wall or another portion of a wall or of tear-resistant tissue of the mammalian body, likewise activated by exerting traction on the second traction element, in particular via its proximal end.

In another embodiment of the invention that is particularly advantageous, the substantially non-extensible, flexible, and deformable material used for making either the first traction element, or the second traction element, or each traction element, or the or each support element, or all of these elements, is an organic polymer compatible with being implanted in mammalian tissue, the organic material being advantageously selected from polyethylene, polypropylene, and nylon, the presently-preferred material being polypropylene.

Selecting this material is particularly advantageous since it is commercially available at reasonable price in the form of yarns that can be woven or knitted so as to take up the shape of a strip of length and of width that can be defined in independent manner and at will, thus being adapted in practice to each patient. Such strips are generally available in the trade and can be cut to size at will directly by the surgical.

Thus, in a particular variant embodiment, provision can be made for the first support element or each support element, to present the form of a strip of width that is sufficient to achieve certain and reliable support of the organ to be supported. The support element is said to be a width that is "sufficient" when its width ensures that the organ to be supported is supported without risk of rupture or injury to said organ, as might otherwise be the case if the width of the support element were too narrow.

In another variant embodiment of the invention, provision can be made for the first traction element or the second traction element, or both of them, comprises or is constituted by a strip of width that is narrower than the width of the strip of the support element. In particular, said width of the strip of the traction element may be less than or equal to about half the width of the strip of the support element.

It can be understood that, according to another variant embodiment of the invention, the support element can be integral with one of the two traction elements. This is particularly easy to be made since according to an embodiment in the form of strips, it will be sufficient to weave or knit in a single step the support element following, or at the end of, the traction element at one and thereof aimed to be the proximal end, a larger part aimed to constitute the support element.

With this embodiment, each traction element in the form of a strip can be made in knitted woven or non-woven form by conventional textile techniques using yarn, and it is particularly easy to make the said fixing system by forming a plurality of transverse folds at one end of the strip, as in folding a table napkin, and then connecting them together by passing a needle-forming element that can be temporarily or permanently secured to the other end of the strip, as described below with reference to FIGS. 2A, 2B, and 2C.

In yet another particular variant embodiment of the invention, at least one fastener element is provided at each end of each support element, for fastening to at least one proximal end of at least one traction element. In a particularly advantageous embodiment of the invention, the fastener element comprises or is constituted essentially by a slot made in the material of the support element, said slot in a particular embodiment being disposed substantially parallel to the longitudinal edges of said strip. The size of this slot may vary over a wide range. Nevertheless, the slot should have at least a minimum size suitable for passing the proximal end of the traction element in order to enable it to be fastened to the support element. Furthermore, in order to avoid weakening the ends of the strip, it is possible to make at least a fold in each end of the strip, e.g. to form a region of double thickness, as can be seen in FIG. 1, so as to provide mechanical reinforcement.

The traction element can be fastened to the support element very simply, when the traction element and the support element are both made in the form of a non-woven or woven strip made of yarn of the said organic polymer material, after the traction element has been passed through said slot, folded back, and pressed down against a facing surface of the support element, with fastening being achieved at their respective surfaces by natural interlocking, obtaining a Velcro type fastener effect as is well known to the person skilled in the art.

According to another variant embodiment of the invention, the support element may comprise a fastener element, which is not in the shape of a slot but in a form of an orifice of any shape and in particular the simplest being of a circular shape.

Besides, according to another advantageous embodiment of the invention device, this device is foreseen or constructed for the treatment of urinary incontinence in particular of a female mammal, and more particularly of a woman; or for a male mammal, in particular a man. The fastening procedure of the devices according to the invention in the case of a female mammal or in the case of a male mammal will be described farther in this specification, notably when describing the surgical procedure. It has to be noted that when the invention device is foreseen for the support of the urethral bulb of a male mammal, it is preferred that the support element be of larger width than in the case of the support of the urethra of a female mammal.

In a second aspect, the present invention also provides, as an independently patentable novel device, each traction element having a distal end comprising or constituting a fixing or anchor system and being as defined above or as results from the description below given with reference to the drawings which form an integral portion of the present invention and which thus add to the present description.

In a third aspect, the present invention also provides a support and fixing or anchor kit comprising at least one surgical device forming a surgical prosthesis according to any preceding aspect; together with an introducer device advantageously in the form of a penetration trocar, with the presence of a pusher element for pushing the traction element with its distal end comprising or constituting the fixing or anchor system, mounted in compact manner or folded inside the penetration trocar. In a variant embodiment, the trocar or pusher element includes at least one blocking element preventing withdrawal of the traction element in place inside the trocar. By way of example, the diameter of the trocar is 4 millimeters (mm).

In a fourth aspect, the present invention also provides a surgical method for providing support to a mammalian organ in need of support, the method comprising:

a) applying local anesthetic in the vicinity of the organ to be supported on the future path of the prosthesis;

b) making an incision and dissecting tissue facing and on either side by the mammalian organ to be supported;

c) inserting a first introducer device forming a trocar in the passage created by said incision and tissue dissection, to one side of and away from the organ to be supported, and after the introducer device forming a trocar has passed through the relatively tear-resistant support of said mammal, such as bone or appropriate tissue, such as, for example the transverse pelvic or abdominal wall, or also the muscular membrane of the obturated foramen of the pelvis, said trocar-forming introducer device of hollow tubular shape containing internally a said first traction element, and a pusher element;

d) applying thrust to the pusher element so as to cause the end of the first traction element to move out from the introducer device until at least the fixing system of the traction element is released beyond said relatively tear-resistant support;

e) after releasing the fixing system, applying traction in the vicinity of the proximal portion of the traction element, enabling the distal end of the traction element forming the fixing or anchor system to be positioned and opened or deployed by being flattened out, thereby obtaining an "umbrella" positioning that presents a large fixing or anchoring area against said relatively tear-resistant support of said mammal;

f) withdrawing the penetration trocar leaving the anchor system in place pressed against the selected support that can thus act as a fixing point since the size of the fixing or anchor system greatly exceeds the size of the orifice caused by penetration of the trocar;

g) repeating above steps c), d), e), and f) on the other side of the organ so as to introduce a second traction element, preferably identical to the first traction element;

h) when none traction element has been initially foreseen integral with the support element, securing the proximal end of the first or second traction element to a facing fastener element at a first end of an elongate support element so as to apply a first traction movement on the proximal end of the traction element for pre-positioning purposes;

i) performing the same procedure as the preceding steps concerning the other second or first traction element with another facing fastener element provided in the vicinity of a second end of the same elongate support element, until said elongate support element is put under tension in an appropriate position relative to said organ so as to provide the looked-for support of said organ; and j) closing or suturing the incision with appropriate surgical closure means, such as resorbable staples or strand, according to conventional operations.

In a preferred first implementation of the surgical procedure, it is used for treating incontinence in a female mammal, in particular a woman. In this context, the organ to be supported is the urethra, preferably in the vicinity of the portion of the urethra that is close to the bladder. Under such circumstances, it is preferred in the present invention for the distal end of the traction element to bear against the tissue of the pelvic wall, preferably the substantially transverse tissue of the pelvic wall in the portion situated between the urethra and the sides of the female mammal, in particular a woman, above the vaginal wall.

According to a second preferred implementation of the surgical procedure, it is used for treating incontinence in a male mammal, in particular a man. In this context, the organ to be supported is again the urethra, preferably in the vicinity of the urethral bulb. In this context, it is preferred according to the invention that the distal end of the traction element to bear against the tissues of the muscular membrane of the obturated foramen of the pelvis, advantageously in a bilateral manner.

It will be understood that in the context of the present invention, there is no cage-forming anchor system of the kind forming the essential component of the surgical device provided in the inventor's earlier solution described in document FR-A-2 843 876=US-A-2005-0261547, to which the person skilled in the art can usefully refer.

The surgical device of the present invention is particularly simple since in practice, and in the embodiment presently considered as being particularly advantageous, it makes use of a unique concept of strips that are widely available in the trade with a variety of dimensions, and with characteristics of knitted woven or non-woven fabric of various mesh sizes, and at reasonable price.

BRIEF DESCRIPTION OF THE DRAWINGS

Other objects, characteristics, and advantages of the invention appear clearly from the following explanatory description made with reference to the accompanying drawings that show a presently-preferred embodiment of the invention given purely by way of illustration and thus not limiting the scope of the invention in any way.

In the drawings:

FIG. 1 is an exploded view of the main elements of the surgical device forming a surgical prosthesis in a presently-preferred embodiment of the invention, comprising at least a first support element 20 of elongate shape, e.g. here in the form of a strip; at least one first traction element 40, that is advantageously filiform, with its distal end to be modified as shown in FIGS. 2A, 2B, 2C in order to comprise or constitute a first fixing or anchor system 48;

FIGS. 2A, 2B, and 2C show the successive steps in fabricating a fixing or anchor system 48 at the end 44 of each traction element, here given overall reference number 40;

FIG. 2A shows the first step in which the end 46 of the traction element 40 is provided with a fastener tool 106, e.g. in the form of a needle-forming element, while a plurality of folds 49 are formed at the other end 44, as shown, each fold being of a length that is sufficient to be capable of forming a fixing and anchor system 48 that is certain and reliable;

FIG. 2B shows the second step at the beginning of the procedure for perforating the folds 49 substantially in their middles by means of the fastener tool 106;

FIG. 2C shows the third and last step of the procedure whereby the tool 106 perforates the folds then constituting the fixing or anchor system 48, and it can be seen that the system 48 can be made simply using the principle of sewing a stitch with a needle-forming element;

FIG. 3 is an enlarged view showing the traction element shown in FIG. 2C, used here both to constitute the first traction element and the second traction element, with the proximal or free end 46 of the traction element 40 mounted inside a fastener tool 106 in the form of a tubular needle and provided with a position-blocking element 108, and with its distal end 44 presenting the folds then constituting the fixing or anchor system 48;

FIG. 4 is a diagram showing the introducer device 100 as a whole, comprising firstly a trocar 102 having inserted therein the traction element 40 or 140 together with its fastener tool 106; and secondly a pusher element 104 preventing the strip being withdrawn;

FIG. 5 is a diagram showing the step of pushing the end 44 of the traction element 40 so as to expel the fixing or anchor device 48, the pusher element possibly presenting for this purpose an end 104a, e.g. in the form of forks enabling the fixing system 48 to be pushed certainly and reliably out from the trocar 102;

FIG. 6 is a diagram showing a first traction element 40 and a second traction element 140 being fastened to a support element 20, here by insertion into respective slots 31, 33, with fastening being by folding over and pressing down the free proximal end of each traction element against the surface either of the support element, or else, and as shown, of the traction element;

FIG. 12 is an exploded view of a second embodiment of the main elements of the surgical device according to the invention comprising at least a first support element 220, of elongated shape, for example here in the form of a strip and at least a first traction element 240, that is advantageously filiform with its distal end to be modified as shown in FIGS. 13, 13A to comprise or constitute a first fixing or anchor system 248; similarly to the embodiment shown in FIGS. 1 to 6;

FIGS. 13 and 13A show the successive steps in fabricating a fixing an anchor system 248 at the end 244 of each traction element, here bearing the general reference number 240, similarly to FIGS. 2A to 2C;

FIG. 14 shows a third embodiment of a surgical device according to the invention, in which the support element 320 of elongated shape, for instance here in the form of a strip, is integral with a first traction element 340 made similarly to that of the two first embodiments shown in FIGS. 1 to 12. In this context, it has to be understood that the support element is manufactured in a single step, when manufacturing the traction element and in continuity with it;

FIGS. 15 and 15A show the successive steps of manufacture of the fixing or anchor system 348 at the end 344 of each traction element 340 similarly to FIGS. 2A to 2C;

MORE DETAILED DESCRIPTION

Figure 7:
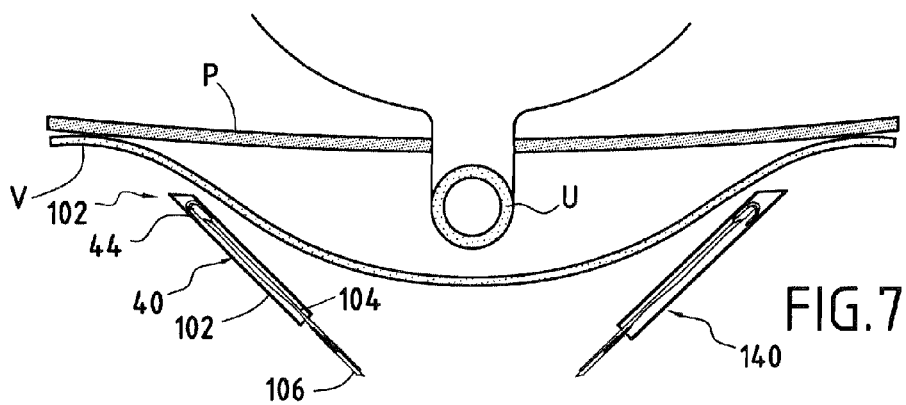
FIG. 7 shows symbolically the two traction elements 40, 140 for putting into place on either side of the organ to be supported, in this case for treating female incontinence and thus serving to support the urethra U.

With reference to FIGS. 1 to 11, and in particular with reference to FIGS. 1 to 6, a surgical device forming a surgical prosthesis of the present invention is given overall reference numeral 10.

The device 10 is for supporting a mammalian organ U in need of support, and in particular here for treating urinary incontinence by supporting the urethra referenced U, and it comprises:

a) at least one first support element 20 comprising an element 22 of elongate shape defining a first end 24 and a second end 26 for exerting a supporting action on said organ; said first element of elongate shape being made at least in part out of a material that is substantially non-extensible, flexible, and deformable; and b) at least one first traction element 40, advantageously a filiform element 42, defining a first end 44 referred to as a distal end and a second end 46 referred to as a proximal end, which elements can be fastened by said proximal end 46 at least temporarily to at least one end 26 of said first elongate support element 20, said distal end 44 being provided to constitute at least one first fixing or anchor system 48, see FIGS. 2C and 3, activated by traction exerted on the first traction element 40, in particular at its proximal end 46 after it has been inserted in a first zone such as P1.

In an advantageous embodiment of the invention, shown in FIGS. 2A, 2B, 2C, and 3, said fixing system 48 provided at the distal end 44 of the traction element 40 includes at least one fold, in practice a plurality of folds 49 of the traction element 40 which, when traction is exerted on the traction element, is deformed or flattened to deploy while imitating an umbrella effect to define an area that is sufficient for fixing or anchoring. An area that is said to be "sufficient" for fixing or anchoring designates an area that ensures that the distal end of the first traction element is fixed or anchored certainly and reliably against the tear-resistant tissue or wall P of the mammalian body, without any risk of tearing said tissue or wall during said traction, or over time with the mammal leading a life without taking any special precautions.

As mentioned above, FIG. 2A shows the first step in fabricating the fixing or anchor system 48, in which the end 46 of the traction element 40 initially provided with a fastener tool 106, e.g. in the form of a substantially tubular needle-forming element provided with a position-blocking element 106 for blocking the end 46 of the traction element in position. At the other end 44 a plurality of folds 49 are made, as shown, each fold 49 being of a length that is sufficient to be capable of constituting a fastening or anchor system 48 that is certain and reliable. In general, each fold may have, for example, a length of about 3 centimeters (cm), to be compared with the width of the traction element which generally does not exceed 0.5 cm.

FIG. 2B shows the second step at the beginning of the procedure for perforating the folds 49 substantially in their middles using the fastener tool 106.

FIG. 2C shows the third and last step of the procedure using the tool 106 to perforate the folds then constituting the fixing or anchor system 48, in which it can be seen that the fixing or anchor system 48 can be made simply, using the principle of sewing a stitch with the help of a needle-forming element.

To make it easier to pass the needle, an orifice may be provided in the folds that can be made by any means, e.g. using a punch.

In another advantageous embodiment of the invention, the first traction element 40 is made at least in part out of a material that is substantially non-extensible, flexible, and deformable. In a particular variant embodiment, the first traction element 40 can be made out of the same material as is used for making the first support element 20.

In another advantageous embodiment of the invention, a second traction element can be provided, preferably of the same design as the first traction element, and thus given the same reference numbers as the first traction element plus 100. This element is thus referenced 140, is likewise filiform, likewise defining a distal first end 144 and a proximal second end 146, being suitable for being fastened via said proximal end 146 at least temporarily to at least one other end 24 of said first elongate support element 20, said distal end 144 of the second traction element 140 also being provided to constitute at least one second fixing or anchor system 148 against another wall or wall portion P2 or against tear-resistant tissue P of the mammalian body, and likewise activated by exerting traction on the second traction element 140, in particular at its proximal end 146.

In a particularly advantageous embodiment of the invention, the substantially non-extensible, flexible, and deformable material used for making either the first traction element, or the second traction element, or each traction element, or the support element(s), or all of these elements, is an organic polymer compatible with being implanted in mammalian tissue, this organic material advantageously being selected from polyethylene, polypropylene, and nylon. The presently-preferred material is polypropylene.

It is particularly advantageous to select this material because it is commercially available at a reasonable price in the form of yarns that can be worked in woven or non-woven or knitted form so as to be presented in the form of a strip, as can clearly be seen in particular in FIGS. 1 to 6, of length and width that can be defined independently, and at will, thus being suitable for being adapted to practically any patient.

Such strips are generally commercially available and can be cut to size at will directly by the surgeon. They also offer the advantage of being capable of being pierced or perforated easily by a fastener tool 106 such as a needle-forming element.

Thus, in a particular variant embodiment, provision can be made for the first support element 20, or each support element, to be in the form of a strip 22 of width that is sufficient to provide certain and reliable support of the organ to be supported. The term "sufficient" when applied to the width of the support element means that the width provides support to the organ for supporting without any risk of rupturing or injuring the organ, as might happen if the width of the support element were too small. For example, the support element 20 in the form of a strip may present a length of about 2.5 cm and a width of about 1 cm.

In another particular variant embodiment of the invention, provision can be made for the first traction element or the second traction element, or both of them, to comprise or be constituted by a strip 42, 142 of width that is smaller than the width of the strip 22 of the support element 20. In particular, the width of the strip 42, 142 of the traction element 40, 140 may be less than or equal to about half the width of the strip of the support element. Thus, the length of each traction element may be about 10 cm, before or after forming the folds 49, the anchor systems 48, 148 e.g. formed as described above on the principle of sewing a stitch by passing a needle through the strip, and presenting a width of no more than about 0.5 cm, i.e. 5 mm.

In yet another particular variant embodiment of the invention, provision is made at each end 24, 26 of each support element 20 for at least one fastener element 30, 32 for fastening to at least one proximal end 46, 146 of at least one traction element 40, 140.

In a particular advantageous embodiment of the invention, this fastener element 30, 32 comprises or is constituted a slot 31, 33 made in the material of the support element 20, said slot 31, 33, see FIG. 1, being disposed in one particular embodiment substantially parallel to the longitudinal edges of said strip 22. The size of this slot may vary over a large range. Nevertheless, the slot should present a minimum size sufficient to allow the proximal end of the traction element to pass therethrough in order to be fastened to the support element.

Figure 11:
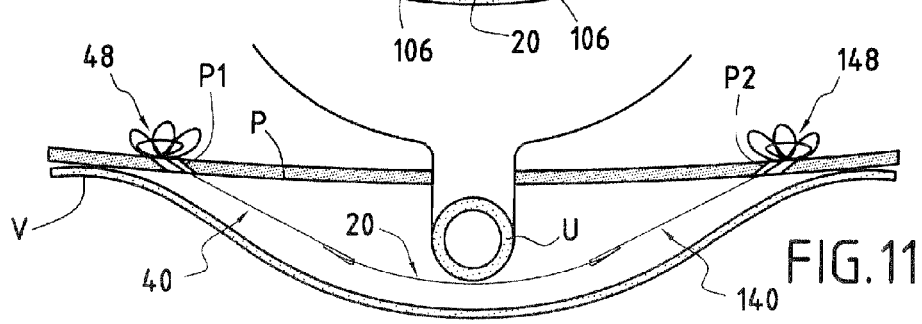
FIG. 11 shows symbolically the end of the surgical procedure at the moment when the surgeon has finished fastening the traction elements 40, 140 to the support element 20, after adjusting traction so as to achieve the appropriate degree of support for the organ that is to be supported, here the urethra.

The traction element 40, 140 can be fastened to the support element 20 very simply, as shown symbolically respectively in FIG. 6 and in FIG. 11. When the traction element 40, 140 and the support element 20 are each formed in a strip of woven or non-woven form using yarns of the said organic polymer material, the surgeon proceeds by inserting the proximal end 46, 146 of the traction element 40, 140 through the respective slots 31 or 33, and then by folding over and pressing down the end 46, 146 of the traction element against the facing surface either of the support element 20, or of the traction element 40, 140, thereby fastening their respective surfaces together by natural interpenetration in the mesh of the woven or non-woven strip, obtaining a fastener effect of the Velcro type, well known to the person skilled in the art, in a manner that is particularly simple and easy to achieve.

A second embodiment of the main elements of the surgical device of the invention is shown under an exploded view in FIG. 12 and is similar to that of FIG. 1.

Thus, it is used the same reference numbers as those of FIG. 1 for the identical or of similar function but increased by 200. Thus, device 220 comprises at least a first support element 220, of elongated shape, for instance here also in the form of a strip, and at least a first traction element 240, advantageously filiform, which distal end will be modified as shown on FIGS. 13, 13A, to include or constitute a first fixing or anchor system 248, similarly to the embodiment of FIGS. 1 to 6. In this embodiment, the fastener element 230, 232 may comprise orifices or slots having a cross-section of any shape but performed here in an easy manner in the shape of orifices or slots of circular cross-section 231, 233. It can be understood that this second embodiment has the same advantages as those shown on FIGS. 1 to 11.

FIGS. 13 and 13A show the successive steps of manufacture of the fixing or anchor system 248 at the end 244 of each traction element, here bearing the general reference number 240 similarly to FIGS. 2A to 2C by the formation of folds 249 at the end 244, see FIG. 15, then their perforation with the needle system 306, which will be then removed, see FIG. 13A.

Figure 16:
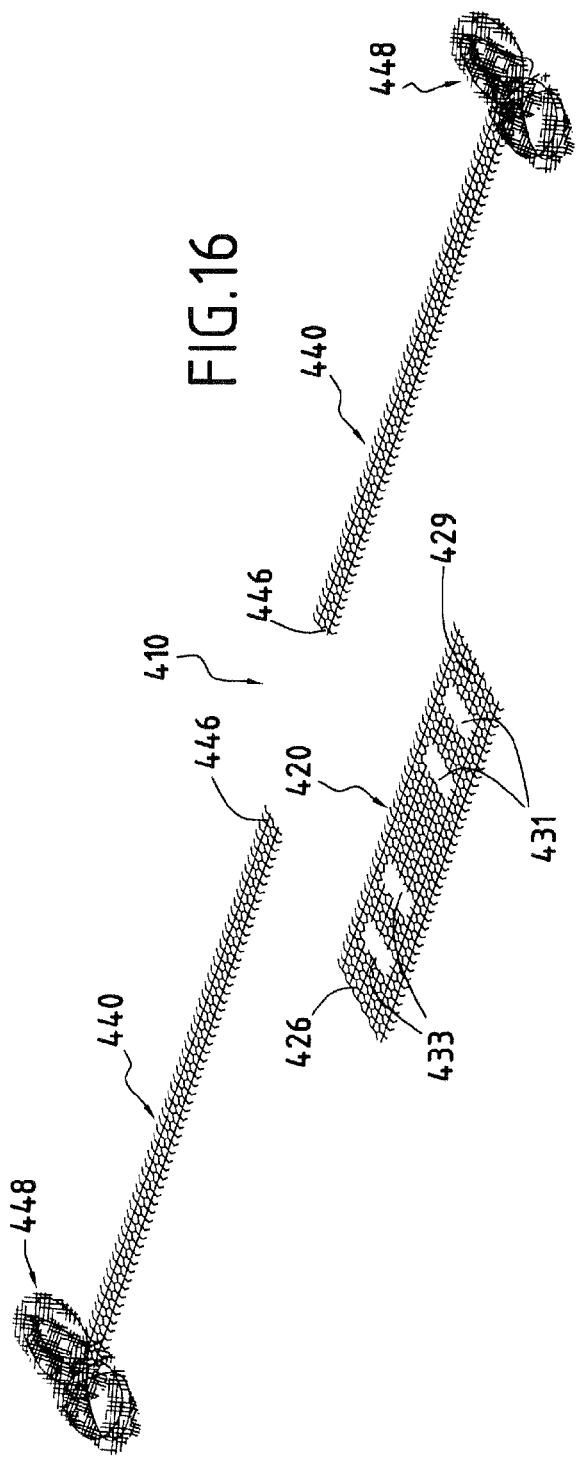
FIG. 16 is an exploded view of a fourth embodiment of the surgical device according to the invention, in which the support element 420 is particularly adapted to perform the support of the urethral bulb of a male mammal, preferably a man, in which the support element is of greater width, and comprises here preferably on each side at least one, and preferably at least two, fastener elements, such as orifices or slots, so as to simplify the fastening procedure of the support element to the traction elements 440, identical or similar to those subject matter of the embodiments shown on FIGS. 1 to 15.
Figure 17:
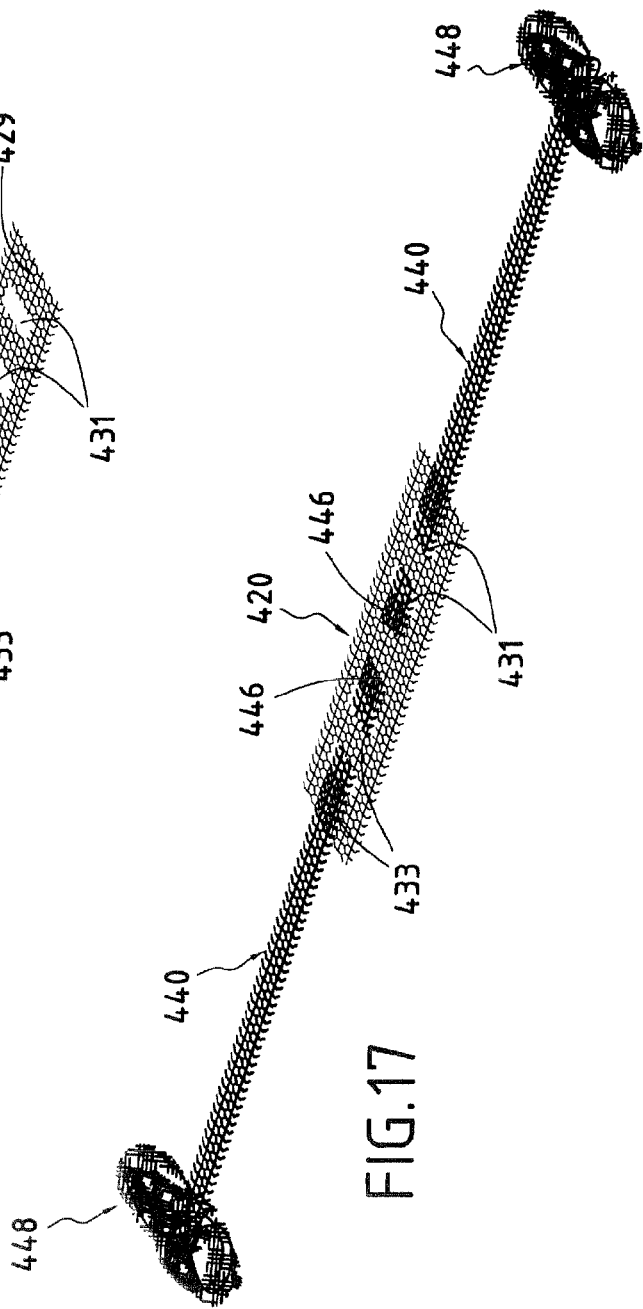
FIG. 17 shows the surgical device of FIG. 16 under a mounted state, enabling to see the easiness of assembling.

FIG. 14 shows a third embodiment of the surgical device according to the invention, in which the reference numbers have been again increased by 100 with regard to the second embodiment of FIG. 12. According to this third embodiment, the support element 320 of elongated shape, for instance here in the form of a strip, is manufactured integral with the first traction element 34C, this first traction element 340 being manufactured similarly to that of two first embodiments shown on FIGS. 1 to 12. In this context, it can be understood that the preferred embodiment where the support element 320 and the traction element 340 are in the form of a woven or knitted strip, the support element 320 is manufactured on a single step when manufacturing the traction element 340 and in continuity thereto. In such an embodiment, the support element 320 can be simplified to comprise, on only one free side, at least one fastener element, for example a hole or slot 333;

FIGS. 15 and 15A show the successive steps of manufacturing of the fixing of anchor system 348 at the end 344 of each traction element 340, by the formation of folds 349, similarly to FIGS. 2A to 2C;

FIG. 16 shows an exploded view of a forth embodiment of the surgical device according to the invention, in which the reference numbers have again been increased by 100, in which the support element 420 is particularly adapted to perform the support of urethral bulb of a male mammal, preferably a man and in such a case, it is preferred that the support element be of a greater width to ensure a firm and reliable support of the male urethral bulb. According to this embodiment, the support element 420 comprises preferably on each side 420, 426 at least one, and again preferably at least two, fastener elements, such as orifices or slots 431 or 433, with the aim to simplify the fastening procedure of the support element with the traction element 440, identical or similar to those subject matter of the embodiments shown on FIGS. 1 to 15;

FIG. 17 shows the surgical device of FIG. 16 in assembled form, enabling to see the easiness of assembling. It will be observed that due to the combination of the two fastener elements 431 or 433 on each side of the support element 420, manufacture for instance here in the form of a woven or knitted strip after insertion of the free end 446, opposite to the fixing or anchor system 448, obtained by the formation of folds and their perforation similarly to the method of manufacture shown on FIGS. 2A, 2B, 2C, it is obtained a fastening safe and reliable of the traction element 440 with the support element 320, without the use of a fastening system complex and hard to manipulate.

Figure 18:
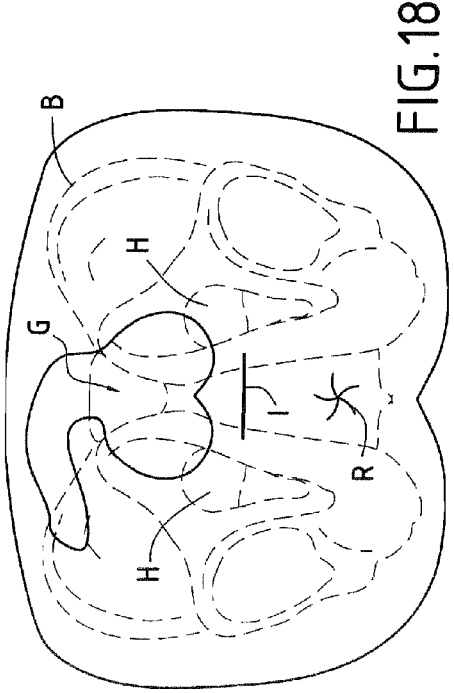
FIG. 18 shows the first step of the surgical procedure for implanting in a male mammal, preferably a man, of the surgical device shown in FIG. 16, showing the transverse incision line I between the rectum and the genital parts, the farther from the rectum.
Figure 19:
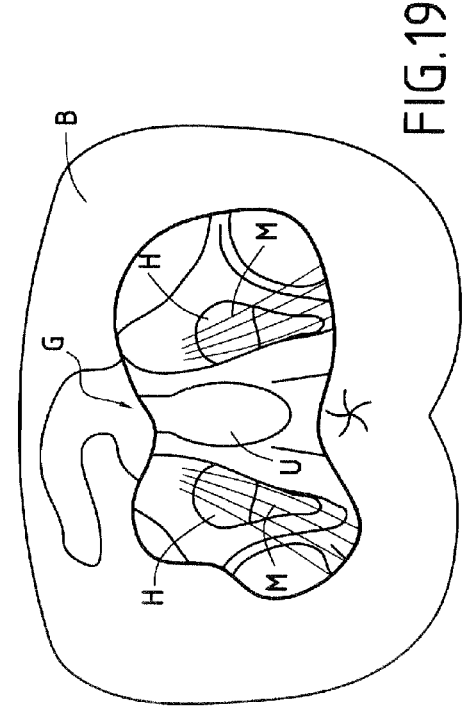
FIG. 19 shows, after moving away the flesh, the obturated foramen of the pelvis, with symbolically each muscular membrane obturating each obturated foramen of the pelvis.

FIG. 18 shows the first step of the surgical procedure of implantation in a male mammal, preferably a man, of the surgical device shown on FIG. 16, showing the transversal incision line I between the rectum R and the genital parts G, the farthest from the rectum R. It is shown on FIG. 18 the pelvis B in shadow spots, as well the obturated foramen H;

FIG. 19 shows the situation obtained, after the step of surgical procedure, after moving away the flesh, enabling to well observe the presence of the obturated foramen H of the pelvis, in a symbolic manner, the access to each muscular membrane M obturating each obturated foramen H of the pelvis B. Urethral bulb U to be supported can be clearly seen with its free access.

Figure 8:
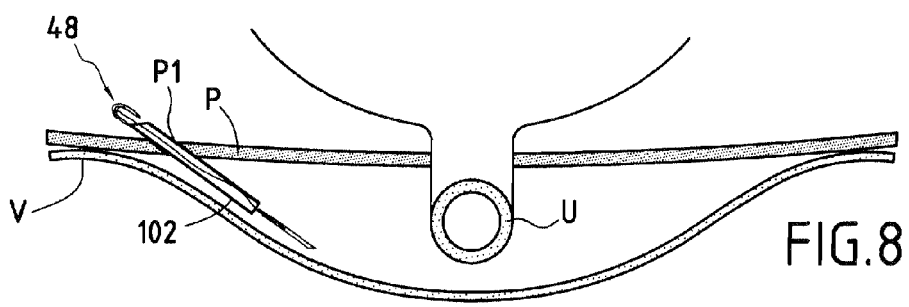
FIG. 8 shows symbolically the insertion of the first traction element passing through an incision and shows dissection formed through a relatively tear-resistant mammalian support, such as a bone, or here tissues of the pelvic wall P.
Figure 9:
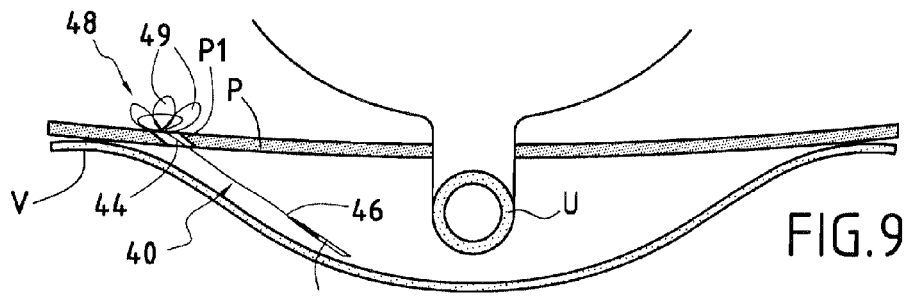
FIG. 9 shows symbolically the step of applying traction enabling the distal end of the traction element to be fastened certainly and reliably against the relatively tear-resistant mammalian support, here the pelvic wall.
Figure 20:
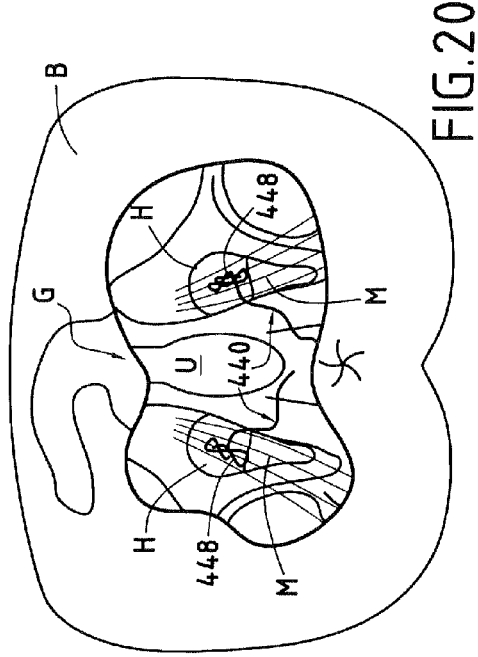
FIG. 20 shows each fixing or anchor system 448 of FIG. 16 in place after perforating the muscular membrane at the level of the obturated foramen, with a perforating trocar, similarly to the putting in place in a female mammal as shown on FIGS. 7 to 9.

FIG. 20 shows the following step of the surgical procedure, similar in its principle to that of the implantation surgery in a female mammal, according to which each fixing or anchor system 440 of FIG. 16 has been put into place through perforation of the muscular membrane M at the level of the obturated foramen H, with the help of a perforating trocar similar to that shown in FIGS. 4, 5, 7, 8, and withdrawal traction to unfold the fixing or anchor system 448 so that it takes the form of an umbrella bearing on a large surface area against the muscular membrane M, similarly to the putting into place in a female mammal as shown on FIGS. 7 to 9, as it is well understood by a surgeon skilled in the art.

Figure 21:
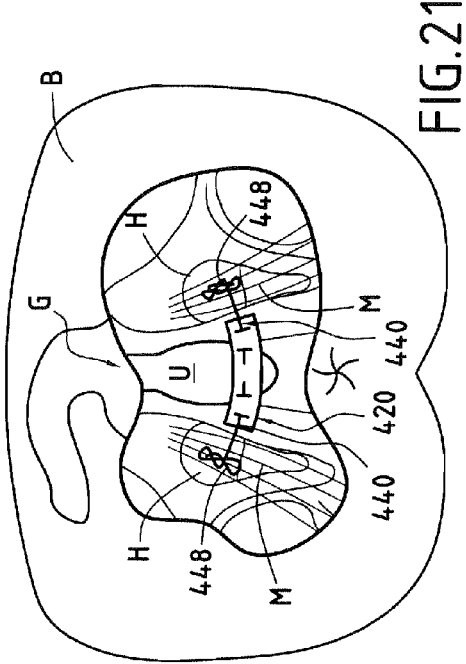
FIG. 21 shows the end of the insertion of the surgical device according to the invention after fastening the support element 420 to the traction element 440, similarly to the fastening position shown on FIG. 17, and traction according to the degree of traction wished by the surgeon.
Figure 22:
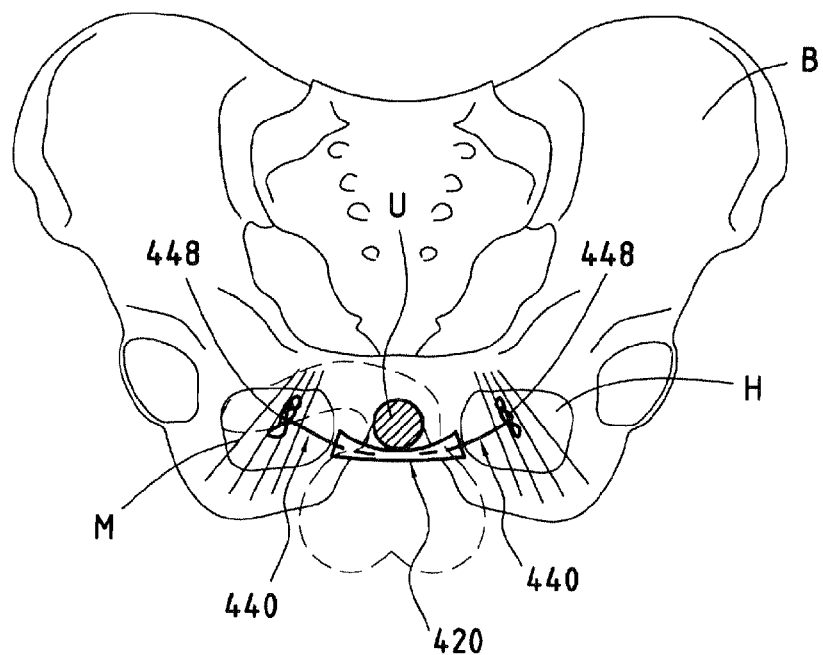
FIG. 22 is a front view of the pelvis representing in a cross-section the urethral bulb at the level of the support with the surgical device according to the invention of FIGS. 16 to 21.

FIG. 21 shows the end of the putting into place in a male mammal, here a man, of the surgical device according to the invention, comprising the step of fastening of the support element 420 on the traction elements 440, in a similar manner to the fastening position shown on FIG. 17, and traction on at least one preferably both traction elements 440, according to the degree of traction, thus of the support of the urethral bulb wished by the surgeon, to treat safely and reliably the problem of male incontinence of a patient of the mammal or patient. The support position of the device is well seen from front and from side on FIGS. 22 and 23.

In a second aspect, the present invention also provides, as an independently patentable novel device, each traction element 40, 240, 340, 440 including a distal end 44, 244, 344, 444 comprising or constituting a fixing or anchor system 48, 248, 348, 448 as defined above, or as results from the following description made with reference to the drawings which form an integral part of the present invention and can thus be used to add to the present description.

In a third aspect, the present invention also provides a support and fixing or anchor kit comprising at least one surgical device 10, 210, 310, 410 forming a surgical prosthesis according to any of the preceding aspects, together with an introducer device (100) advantageously in the form of a penetration trocar (102), with the presence of a pusher element (104) for pushing the traction element 40 or 240, 340, 440 with its distal end comprising or constituting the fixing or anchor system 48 or 248, 348, 448 mounted in compact manner or folded inside the penetration trocar (102). Advantageously, the trocar 102 or a pusher element 104 may include a blocking element preventing withdrawal of the traction element that is in place inside the trocar. Advantageously, an element may be provided that forms a stop abutment 105 against forward thrust of the pusher element 104, so as to avoid penetrating too far after the fixing or anchor device 48 has moved out from the trocar 102, as shown in FIG. 5.

Figure 10:
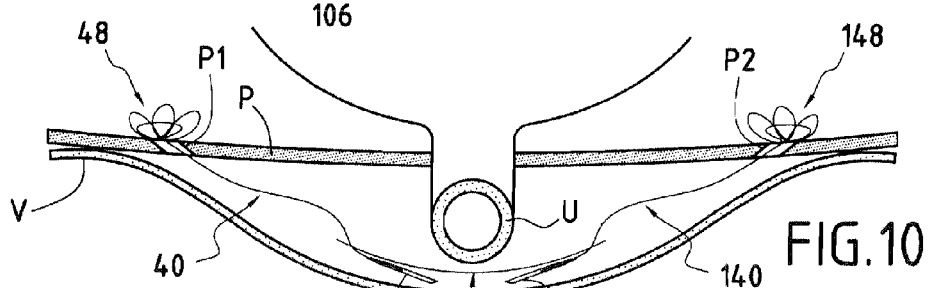
FIG. 10 shows symbolically the instant when the surgeon has put the second traction element 140 into place and has fastened the first traction element and the second traction element to the first support element 20, prior to adjusting the traction in order to achieve appropriate support for the organ to be supported, in this case the urethra U.

In a fourth aspect, the present invention also provides a surgical method for providing support to a mammalian organ in need of support, the method comprising:

a) applying local anesthetic in the vicinity of the organ U to be supported on the future path of the prosthesis, a conventional operation that is naturally not shown;

b) making an incision I and dissecting tissue facing and on either side by the mammalian organ U to be supported, a conventional operation that is not shown;

c) inserting a first introducer device 100 forming a trocar 102 in the passage created by said incision and tissue dissection, to one side of and away from the organ to be supported, and after the introducer device forming a trocar 102 has passed through the relatively tear-resistant support of said mammal, such as bone or appropriate tissue, such as, for example the transverse pelvic or abdominal wall P, e.g. in position P1, or also the muscular membrane M of the obturated foremen H of the pelvis, by passing through a perforation, the trocar-forming introducer device of hollow tubular shape containing internally a said first traction element 40, 240, 340 or 440, and a pusher element 104;

d) applying thrust to the pusher element 104 so as to cause the end of the first traction element 40, 240, 340 or 440 to move out from the introducer device until at least the fixing system 48, 248, 348, 448 of the traction element is released beyond said relatively tear-resistant support P;

e) after releasing the fixing system 48, 248, 348, 448, applying traction in the vicinity of the proximal portion of the traction element, enabling the distal end of the traction element forming the fixing or anchor system to be positioned and opened or deployed by being flattened out, thereby obtaining an "umbrella" positioning that presents a large fixing or anchoring area against said relatively tear-resistant support P of said mammal, as shown in FIG. 8;

f) withdrawing the penetration trocar 102 leaving the anchor system in place pressed against the selected support P that can thus act as a fixing point since the size of the fixing or anchor system greatly exceeds the size of the orifice caused by penetration of the trocar, as shown in FIG. 9;

g) repeating above steps c), d), e), and f) on the other side of the organ so as to introduce a second traction element 140, 240, 340, 440, preferably identical to the first traction element 40, e.g. in the zone P2;

h) when none traction element is initially foreseen integral to the support element, using the tool 106 to secure the proximal end of the first or second traction element to a facing fastener element 30 at a first end of an elongate support element 20 so as to apply a first traction movement on the proximal end of the traction element for pre-positioning, as shown in FIG. 10;

i) performing the same procedure as the preceding steps concerning the other second 140 or first traction element with another facing fastener element 32 at a second end of the same elongate support element, until said elongate support element is put under tension in an appropriate position relative to said organ so as to provide the looked-for support of said organ, as shown in FIG. 11, removing the tools 106 and the blocking elements 108; and j) closing or suturing the incision with appropriate surgical closure means, such as resorbable staples or stand, according to conventional operations that are not shown.

With reference now to FIG. 14, the support element can be manufactured integral or mono-bloc with the first traction element, such as traction element 40, 140 or 240. In such a case, the surgical method is simplified since step H is to be made only with the second traction element since the first traction is already integral with the support element. Thus, steps h and i are performed in a single step.

In a preferred first implementation of this surgical method, it is used for treating incontinence in a female mammal, in particular in a woman. In this context, the organ to be supported is the urethra U, preferably close to the vicinity of the portion of the urethra that is close to the bladder, as shown in FIGS. 7 to 11. In this context, it is preferable in the present invention for the distal end of the traction element to bear against the tissue of the pelvic wall P, preferably against substantially transverse tissue of the pelvic wall in its portion situated between the urethra and the sides of the female mammal, in particular a woman, above the vaginal wall, as shown in FIGS. 7 to 11.

The person skilled in the art understands that with the surgical procedure of the invention, at the end of step g), the two side anchors are in place and the two free ends 46, 146 of the traction elements 40, 140 extend through the surgical incision.

It is easy for the surgeon to pass the free ends 46 or 146 of the traction elements and to position the support element 20 by causing the free ends to slide through the slots 31, 33. The invention thus enables the support element 20 or prosthesis to be positioned ideally by very simple adjustment of tension and makes it possible to reduce excess tension by pulling back lightly the support element 20. It is also possible to envisage surgical retouching in the following ten days in order to relax traction that is too strong, which is very difficult or much more hazardous when using prior surgical procedures.

After finally selecting the ideal position, the operator cuts away excess length from each traction element 40 or 140, preferably leaving about 2 cm beneath the support element 20 for folding back the free end 46 or 146 to 180° along the traction element 40 or 140 as shown in FIG. 6 or in FIG. 11, without making any stitches since the invention enables sufficient fixing to be obtained by the woven or non-woven strip structure of the anchor element or of the support element 20, using a Velcro type effect, made possible by the bonding properties of the mesh of the prosthesis. Natural healing will block the prosthesis finally in place by fibrosis within about two weeks.

According to the embodiment shown on FIGS. 16 to 23, the invention also relates to a surgical method for performing the support of an organ to be supported of a male mammal, in particular a man. In this case, it will generally be treated the male incontinence, in particular after operation of the prostate. In this context, the organ to be supported is the urethral bulb U, see FIG. 19 to 23, preferably between the obturated foramen H of the pelvis B, namely between the ischion bones of the pelvis B, as shown on FIGS. 18 to 23. Again, in this context, it is preferred according to the invention that the distal end 448 of each traction element 440 bears on the tissues of the muscular membrane M obturating the obturated foramen H of the pelvis B, as clearly seen on FIGS. 20 to 23.

Figure 23:
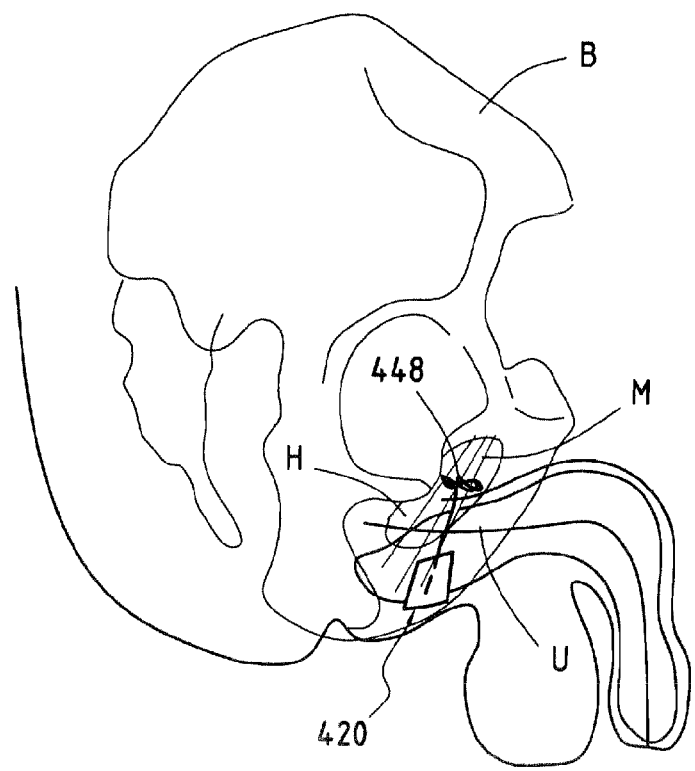
FIG. 23 is a side-view of the pelvis showing the surgical device according to the invention of FIGS. 16 to 21 in support position, enabling to well see the fixing and anchor system 448 to bear, here in the shape of an umbrella, on the muscular membrane M obturating the obturated foramen H of the pelvis and inside of the foramen or aperture, therefore opposite to the support element 440.

The man skilled in the art will understand that with the invention surgical procedure, such as defined for a female mammal, preferably a woman, and for a male mammal, the fastening procedure with the support element will be simplified as shown on FIGS. 20 and 23 in view of a greater access to the urethral bulb U in man, with respect to the interior of the vagina of a woman, by making a substantially horizontal incision between the rectum R and the genital parts G, the farthest away from the rectum R. In addition, the fastening step can be performed easily by the presence of two fastener elements constituted here by two orifices or slots 431, 433 set aside at each end of the support element such as a strip and which enables to perform a fastening effect very efficient between the support element and the traction element, without necessarily requiring to perform the folding foreseen in the context of the embodiments for the woman and without foreseeing any suture. Obviously, this solution can also be performed in the context of the support of the feminine urethra.

The invention is not limited to the support of the feminine urethra or of the masculine urethral bulb, but can be used for other ptosed organs, for instance the genital prolapsus of woman, optionally the support of the bladder or even of the rectum.

In the context of the invention, use of a postoperative probe is not recommended since it has no useful effect and can be a source of infection. Procedures prior to the invention have generally required the bladder to be probed because of deeper anesthesia and pains, risks which are avoided by the invention. The invention thus provides a prosthesis of very simple design, and simplification to the surgical procedure that constitutes advantages that are particularly unexpected and non-obvious for the person skilled in the art.

The invention naturally covers all means constituting technical equivalents to the means described and shown in the accompanying figures which form an integral portion of the present invention and thus add to the present description.

Each characteristic that appears novel relative to any state of the art is claimed as such concerning its function and as general means.

What is claimed is:

1. A surgical device forming a surgical prosthesis, for supporting a mammalian organ in need of support, the device comprising:
   a) at least one elongated support element having a first end and a second end for exerting a supporting action on said organ the support element being made, at least in part, out of a material that is substantially non-extendable, flexible, and deformable;
   b) a first filiform traction element having a distal end and a proximal end, the proximal end of the first traction element can be fastened to the first end of said support element, said distal end of the first traction element having a first fixing system, the first fixing system integral with the distal end of the first traction element and comprising a plurality of folds in the distal end of the first traction element and the proximal end of the first traction element having perforated the folds to form the first fixing system, such that when traction is exerted on the proximal end of the first traction element, the first fixing system deploys to provide an umbrella effect so as to define an area that is sufficient for anchoring; and
   c) a second filiform traction element, having a distal end and a proximal end, the proximal end of the second traction element can be fastened to the second end of the support element and the distal end of the second traction element having a second fixing system for anchoring.

2. A device according to claim 1, wherein the folds are perforated by a needle-forming element attached to the proximal end of the first traction element.

3. A device according to claim 1, wherein the first traction element is made, at least in part, out of the same material used for making the support element.

4. A device according to claim 1, wherein the second fixing system is formed in the same way as the first fixing system.

5. A device according to claim 1, wherein either the first traction element, or the second traction element, or each traction element, is made of the same material used to make the support element and the material is an organic polymer compatible with being implanted in mammalian tissue, the organic polymer is polyethylene, polypropylene, or nylon.

6. A device according to claim 1, wherein the first support element is a strip of width that is sufficient to achieve support of the organ to be supported.

7. A device according to claim 1, wherein the first traction element or she second traction element, or both of them, comprises a strip of a width that is narrower than a width of the support element.

8. A device according to claim 1, wherein at least one fastener element is provided at each end of the support element, for fastening to the proximal end of the first and second traction element.

9. A device according to claim 8, wherein the fastener element comprises a slot made in the material of the support element, said slot being disposed substantially parallel to longitudinal edges of the support element.

10. A device according to claim 1, wherein the first and second traction element and the support element are each formed by a woven or non-woven strip made from yarns of organic polymer material; the first and second traction element and the support element are fastened together using at least one fastener element by pressing the first and second traction element against a facing surface of the support element, causing respective surfaces to be fastened together by natural interpenetration.

11. The device of claim 1 wherein the proximal end of the second traction element is integral with the second end of the support element.

12. The device of claim 1 wherein the folds in the distal end of the first traction element are formed by coiling the distal end of the first traction element.

13. The device of claim 1 wherein the folds in the distal end of the first traction element are formed by serpentine folds in the distal end of the first traction element.

14. A support and fixing kit comprising at least one surgical device for forming a surgical prosthesis as defined in claim 1; together with a first and second introducer device, each in the form of a penetration trocar, the trocar having a pusher element for pushing the distal end of the traction element with the fixing system, folded inside the penetration trocar.

15. A surgical method for providing support to a mammalian organ in need of support, the method comprising:
   a) applying local anesthetic in the vicinity of the organ to be supported on the future path of a prosthesis;
   b) making an incision and dissecting tissue facing and on either side by the mammalian organ to be supported;
   c) inserting a first introducer device, forming a trocar, in the passage created by said incision and tissue dissection, to one side of and away from the organ to be supported, and after, the introducer device forming a trocar is passed through a relatively tear-resistant support of said mammal, said trocar-forming introducer device of hollow tubular shape containing internally a first traction element, and a pusher element the first traction element having a proximal end and a distal end, the distal end having a first fixing system integral therewith, the first fixing system comprising a plurality of folds in the distal end of the first traction element and the proximal end of the first traction element having perforated the folds to form the first fixing system;
   d) applying thrust to the pusher element so as to cause a distal end of a first traction element to move out from the introducer device until the first fixing system of the first traction element is released beyond said relatively tear-resistant support;
   e) after releasing the first fixing system, applying traction in the vicinity of the proximal end of the first traction element, enabling the first fixing system to be positioned and deployed by being flattened out, thereby obtaining an "umbrella" positioning that presents a large anchoring area against said relatively tear-resistant support of said mammal;
   f) withdrawing the penetration trocar leaving the first fixing system in place pressed against the tear-resistant support that can thus act as a fixing point since the size of the first fixing system greatly exceeds the size of the orifice caused by penetration of the trocar;

g) repeating above steps c), d), e), and f) on the other side of the organ so as to introduce a second traction element, identical to the first traction element;

h) securing the proximal end of the first traction element to a first fastener element at a first end of an elongate support element so as to apply a first traction movement on the proximal end of the traction element for prepositioning purposes;

i) performing the same procedure as step h concerning the second traction element with a second fastener element provided at a second end of the elongate support element, until said elongate support element is put under tension in an appropriate position relative to said organ so as to provide the desired support of said organ; and j) closing or suturing the incision with appropriate surgical closure means.

16. The surgical method of claim 15 for treating Incontinence in a female mammal.

17. The surgical method of claim 16, wherein the distal end of the first and second traction element bears against the tissue of the pelvic wall, in the portion situated between the urethra and the sides of the female mammal above the vaginal wall.

18. The surgical method of claim 15, for treating incontinence in a male mammal, the organ to be supported being the urethra, the support being performed in the vicinity of the urethral bulb.

19. The surgical method of claim 18, wherein the distal end of the first and second traction element bears against the tissues of the muscular membrane of the obturated foramen of the pelvis.

20. A surgical device forming a surgical prosthesis, for supporting a mammalian organ in need of support, the device comprising:

a) at least one elongated support element having a first end and a second end for exerting a supporting action on said organ, the support element being made, at least in part, out of a material that is substantially non-extendable, flexible, and deformable; the support element is formed by a woven or non-woven strip made from yarns of organic polymer material compatible with being implanted in mammalian tissue;

b) a first filiform traction element having a distal end and a proximal end, the first traction element is formed by a woven or non-woven strip made from yarns of organic polymer material compatible with being implanted in mammalian tissue, the proximal end of the first traction element can be fastened to one end of the support element, by passing the proximal end of the first traction element through the support element, said distal end of the first traction element having a first fixing system, the first fixing system being integral with the distal end of the first traction element and comprising folds in the distal end of the first traction element, such that when traction is exerted on the proximal end of the traction element, the folds of the first fixing system deploy to provide an umbrella effect so as to define an area that is sufficient for fixing; and c) a second filiform traction element, having a distal end and a proximal end, the second traction element is formed by a woven or non-woven strip made from yarns of organic polymer material compatible with being implanted in mammalian tissue, the proximal end of the second traction element can be fastened to the other end of the support element, by passing the proximal end of the second traction element through the support element, the distal end of the traction element having a second fixing system.

21. The device of claim 20, wherein the proximal end of the first and second traction element and the support element are fastened together by pressing the proximal end of the first and second traction element against a facing surface of either the support element or the first or second traction element, causing their respective surfaces to be fastened together by natural interpenetration.

22. A device according to claim 20, wherein the folds in the distal end of the first traction element are fastened together, by being perforated by a needle-forming element attached to the proximal end of the first traction element so as to form the fixing system.

23. A device according to claim 20, wherein the organic polymer material is selected from the group consisting of polyethylene, polypropylene, and nylon.

24. A device according to claim 20, wherein the second fixing system is formed from folds of said strip in the distal end of the second traction element.

25. A device according to claim 20, wherein the support element is a strip of width that is sufficient to achieve support of the organ to be supported.

26. A device according to claim 20, wherein the first traction element or the second traction element, or both of them, comprises a strip of a width that is narrower than a width of the support element.

27. A surgical device forming a surgical prosthesis, for supporting a mammalian organ in need of support, the device comprising:

a) at least one elongated support element having a first end and a second end for exerting a supporting action on said organ, the support element being made, at least in part, out of a material that is substantially non-extendable, flexible, and deformable; and a first slot made in the material at first end and a second slot made in the material at the second end of the support element;

b) a first filiform traction element having a distal end and a proximal end, the proximal end of the first traction element can be fastened to one end of the support element, by passing the proximal end of the first traction element through the first slot, said distal end of the first traction element having a first fixing system, the first fixing system being integral with the distal end of the first traction element and comprising folds in the distal end of the first traction element, such that when traction is exerted on the proximal end of the traction element, the folds of the first fixing system deploy to provide an umbrella effect so as to define an area that is sufficient for fixing;

c) a second filiform traction element, having a distal end and a proximal end, the proximal end of the second traction element can be fastened to the second end of the support element by passing the proximal end of the traction through the second slot, the distal end of the traction element having a second fixing system; and d) the first traction element, second traction element and the support element are each formed by a woven or nonwoven strip made from yarns of organic polymer material, the proximal end of the first and second traction element and the support element are fastened together by pressing the proximal end of the first and second traction element against a strip facing surface of either the support element or the first or second traction element, causing their respective surfaces to be fastened together by natural interpenetration.

28. A support and fixing kit comprising ac least one surgical device for forming a surgical prosthesis as defined in claim 20; together with a first and second introducer device, each in the form of a penetration trocar, the trocar having a pusher element for pushing the distal end of the traction element with the fixing system, folded inside the penetration trocar.

29. A surgical method for providing support to a mammalian organ in need of support, the method comprising:
   a) applying local anesthetic in the vicinity of the organ to be supported on the future path of a prosthesis;
   b) making an incision and dissecting tissue facing and on either side by the mammalian organ to be supported;
   c) inserting a first introducer device, forming a trocar, in the passage created by said incision and tissue dissection, to one side of and away from the organ to be supported, and after, the introducer device forming a trocar is passed through a relatively tear-resistant support of said mammal, said trocar-forming introducer device of hollow tubular shape containing internally a first traction element, and a pusher element; the first traction element having a proximal end and a distal end, the distal end having a first fixing system integral therewith and comprising a plurality of folds in the distal end of the first traction element;
   d) applying thrust to the pusher element so as to cause a distal end of a first traction element to move out from the introducer device until the first fixing system of the first traction element is released beyond said relatively tear-resistant support;
   e) after releasing the first fixing system, applying traction in the vicinity of the proximal end of the first traction element, enabling the first fixing system to be positioned and the folds to be deployed by being flattened out, thereby obtaining an "umbrella" positioning that presents a large anchoring area against said relatively tear-resistant support of said mammal;
   f) withdrawing the penetration trocar leaving the fixing system in place pressed against the tear-resistant support that can thus act as a fixing point since the size of the fixing system greatly exceeds the size of the orifice caused by penetration of the trocar;
   g) repeating above steps c), d), e), and f) on the other side of the organ so as to introduce a second traction element, identical to the first traction element;
   h) securing the proximal end of the first traction element to a first fastener element at a firs: end of an elongate support element so as to apply a first traction movement on the proximal end of the traction element for pre-positioning purposes;
   i) performing the same procedure as step h concerning the second traction element with a second fastener element provided at a second end of the elongate support element, until said elongate support element is put under tension in an appropriate position relative to said organ so as to provide the desired support of said organ, the first traction element, second traction element, and the support element are formed by a woven or non-woven strip made from yarns of organic polymer material, the proximal end of the first and second traction element and the support element are fastened together by pressing the proximal end of the first and second traction element against a strip facing surface of either the support element or the first or second traction element, causing their respective surfaces to be fastened together by natural interpenetration; and
   j) closing or suturing the incision with appropriate surgical closure means.

30. The surgical method of claim 29, for treating incontinence in a female mammal.

31. The surgical method of claim 29, wherein the distal end of the first and second traction element bears against the tissue of the pelvic wall, in the portion situated between the urethra and the sides of the female mammal above the vaginal wall.

32. The surgical method of claim 29, for treating incontinence in a male mammal, the organ to be supported being the urethra, the support being performed in the vicinity of the urethral bulb.

33. The surgical method of claim 32, wherein the distal end of the first and second traction element bears against the tissues of the muscular membrane of the obturated foramen of the pelvis.

* * * * *